US00PP23254P2

(12) United States Plant Patent
Meilland

(10) Patent No.: US PP23,254 P2
(45) Date of Patent: Dec. 18, 2012

(54) HYBRID TEA ROSE PLANT NAMED 'MEIMONKEUR'

(50) Latin Name: *Rosa hybrida*
Varietal Denomination: cv. Meimonkeur

(75) Inventor: Alain A. Meilland, Antibes (FR)

(73) Assignee: CP Delaware Inc., Wilmington, DE (US)

( * ) Notice: Subject to any disclaimer, the term of this patent is extended or adjusted under 35 U.S.C. 154(b) by 0 days.

(21) Appl. No.: 13/137,452

(22) Filed: Aug. 17, 2011

(51) Int. Cl.
*A01H 5/00* (2006.01)

(52) U.S. Cl. ..... Plt./130
(58) Field of Classification Search ..... Plt./130
See application file for complete search history.

*Primary Examiner* — Annette Para
(74) *Attorney, Agent, or Firm* — Buchanan Ingersoll & Rooney P.C.

(57) ABSTRACT

A new and distinct Hybrid Tea rose plant is provided that forms abundantly and substantially continuously attractive red-purple very double blossoms with substantially lighter non-uniform red-purple coloration on the under surface and an anise fragrance. The growth habit is bushy, and strong vegetation is formed. The vegetation is dense and bears a glossy aspect on the upper surface. No particular disease problem has been observed. The plant is particularly well suited for providing attractive ornamentation in parks and gardens.

1 Drawing Sheet

Figures 1, 2, 3, 4, 5, 6, 7, 8, 9, 10, 11, 12, 13, 14, 15, 16:
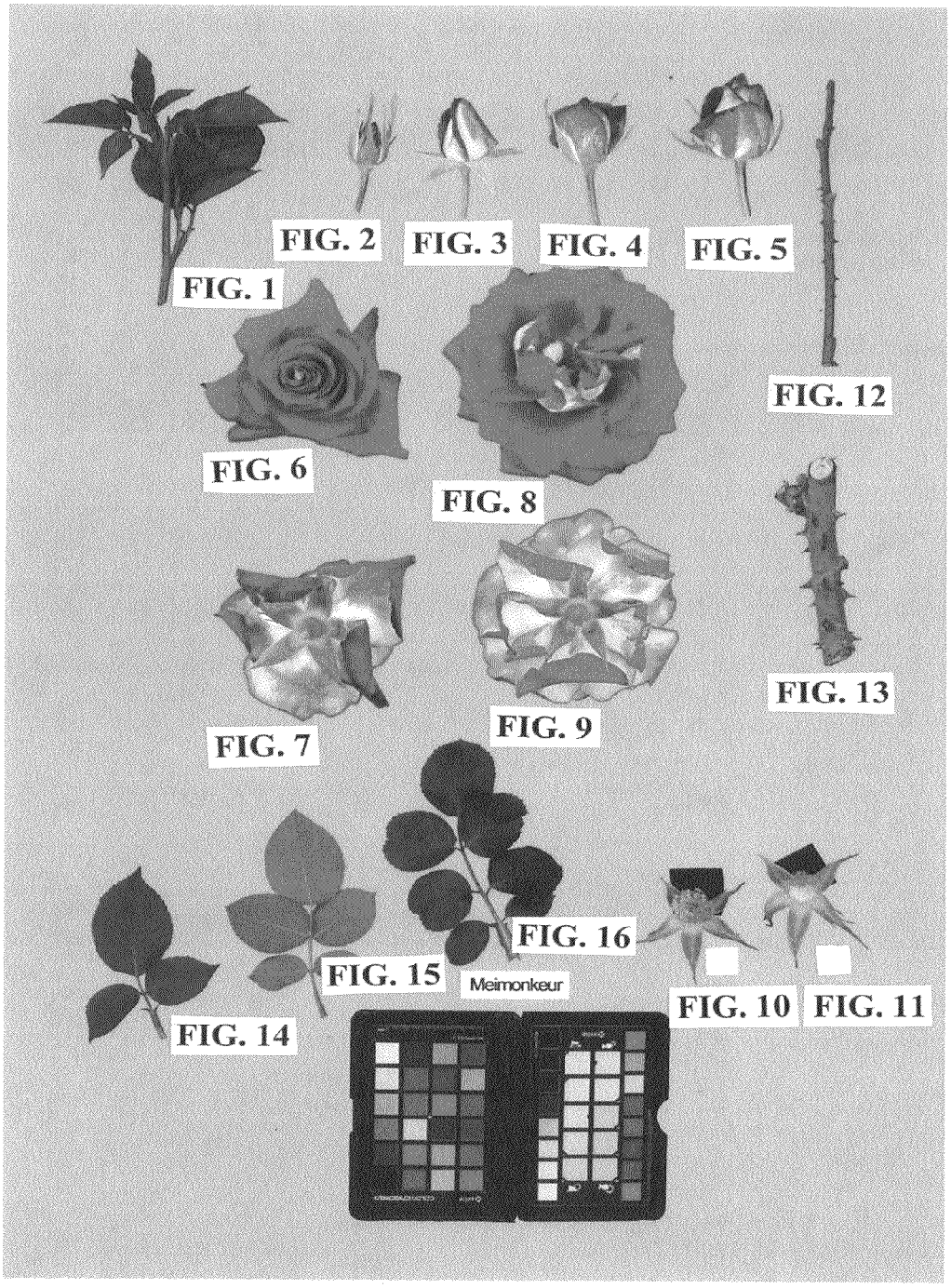

Botanical/commercial classification: *Rosa hybrida*/Hybrid Tea Rose Plant.

Varietal denomination: cv. Meimonkeur.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Meipierar' variety (U.S. Plant Pat. No. 7,622) and 'Meivildo' variety (U.S. Plant Pat. No. 6,895). The male parent (i.e., the pollen parent) was the product of the cross of the 'Meicapula' variety (non-patented in the United States) and the 'Meinuzeten' variety (U.S. Plant Pat. No. 4,224).

The parentage of the new variety can be summarized as follows:

('Meipierar'×'Meivildo')×('Meicapula'× 'Meinuzeten').

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays a bushy growth habit with strong vegetation,
(b) forms in abundance on a substantially continuous basis attractive red-purple very double blossoms with substantially lighter non-uniform red-purple coloration on the under surface which display an anise fragrance,
(c) exhibits attractive dense glossy medium green foliage, and
(d) is particularly well suited for providing attractive ornamentation in parks and gardens.

The new variety well meets the needs of the horticultural industry and can be grown to advantage in the landscape where attractive ornamentation is to be provided.

The new variety can be readily distinguished from its ancestors. For instance, the bicolored red-purple blossom coloration of the new variety is considerably different from that of its ancestors. More specifically, the 'Meipierar' variety forms cream white blossoms, the 'Meivildo' variety forms neyron pink blossoms, the 'Meicapula' variety forms pink blossoms, and the 'Meinuzeten' variety forms orange-red blossoms.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meimonkeur'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately 1-½ years of age and were observed during June while budded on *Rosa laxa* understock and growing outdoors at Le Cannet des Maures, Var, France. Standard colors are presented at the bottom of the photograph for comparative purposes.

FIG. 1—illustrates a specimen of a young shoot;

FIG. 2—illustrates a specimen of a floral bud at the opening of the sepals;

FIG. 3—illustrates a specimen of a floral bud wherein the sepals are fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of 1-½-year-old plants during June which were budded on *Rosa laxa* understock and growing outdoors at Le Cannet des Maures, Var, France.

Class: Hybrid Tea.

Plant:

*Growth habit*.—Bushy.

Branches:

*Color*.—Young stems: near Green Group 137D. Adult wood: near Green Group 137D.

*Thorns*.—On young stems: small prickles: configuration: with an obovate base. quantity: approximately 1 on average on a stem length of 10 cm. length: approximately 0.1 cm on average. color: near Red Group 47D. long prickles: configuration: with an ovate base. quantity: approximately 8 on average on a stem length of 10 cm. length: approximately 0.8 cm on average. color: near Yellow-Green Group 147C. On adult stems: small prickles: quantity: commonly none are present. long prickles: configuration: elongated and curved downwards on the upper surface, concave on the under surface, and with an ovate base. quantity: approximately 9 on average on a stem length of 10 cm. length: approximately 0.7 cm on average. color: near Greyed-Orange Group 165B.

Leaves:

*Stipules*.—Adnate, pectinate, rather broad, approximately 1.6 cm in length on average, approximately 0.4 cm in width on average, near Yellow-Green Group 147C on the upper surface, and near Yellow-Green Group 146C on the under surface.

*Petioles*.—Upper surface: near Yellow-Green Group 147B in coloration. Under surface: near Yellow-Green Group 146C in coloration. Texture: non-glandular on the upper surface, and commonly without prickles on the under surface.

*Rachis*.—Upper surface: near Yellow-Green Group 147B in coloration. Under surface: near Yellow-Green Group 146C in coloration.

*Leaflets*.—Number 3, 5 and 7 (most often). Shape: generally oval with an acuminate tip and a rounded base. General appearance: dense with a glossy aspect on the upper surface. Serration: small and single (as illustrated). Texture: physically firm and leathery. Color (young foliage): upper surface: near Green Group 135B. under surface: near Yellow-Green Group 146C. Color (adult foliage): upper surface: near Green Group 139A. under surface: near Yellow-Green Group 146C.

Inflorescence:

*Number of flowers*.—Commonly 1 to 3 blossoms per stem.

*Peduncle*.—Tomentose, approximately 8 to 9 cm in length on average, approximately 0.4 cm in diameter on average, and near Yellow-Green Group 146C in coloration.

*Sepals*.—Upper surface: tomentose and near Yellow-Green Group 147C in coloration. Under surface: smooth and near Yellow-Green Group 146B and Yellow-Green Group146C in coloration. Shape: generally upright at the base. Size: approximately 3.5 cm in length on average, and approximately 1.1 cm in width at the widest point on average.

*Buds*.—Shape: substantially elongated. Size: large. Length: approximately 4 cm on average. Width: approximately 2.8 cm at the widest point on average. Color as calyx breaks: upper surface: near Red-Purple Group 60B. under surface: near Red-Purple Group 62C suffused with near Red-Purple Group 66D.

*Flower*.—Shape: cup-shaped. Diameter: approximately 11 to 13 cm on average. Color (in the course of opening): upper surface: near Red-Purple Group 63A suffused with near Red Group 46A and 46B. under surface: near Red-Purple Group 62C suffused with near Red-Purple Group 66D. Color (open flower): upper side: near Red-Purple Group 61C. under side: near Red-Purple Group 61C suffused with near Red-Purple Group 64C. Fragrance: medium and resembles anise. Petal number: approximately 50 to 55 on average under normal growing conditions. Petal shape: with a substantially rounded tip and an obtuse base. Petal texture: leathery and somewhat firm. Petal length: approximately 6 to 6.5 cm on average. Petal width: approximately 5.5 to.6 cm on average. Petal arrangement: imbricated, and without petaloids. Petal drop: good with the petals commonly detaching cleanly before drying. Stamen number: approximately 146 on average. Anthers: regularly arranged around the styles, approximately 0.2 cm in size on average, and near Yellow-Orange Group 15D in coloration. Filaments: approximately 0.9 to 1 cm in length on average, and near Red Group 45D in coloration. Pistils: approximately 97 on average. Stigmas: approximately 0.7 cm in size on average, and near White Group 155D in coloration. Styles: approximately 0.1 cm in length on average, and near Red Group 45D in coloration. Receptacle: smooth, funnel-shaped in longitudinal section, approximately 0.5 cm in length on average, approximately 0.7 cm in width on average at the widest point, and near Yellow-Green Group 146C in coloration.

Development:

*Vegetation*.—Strong.

*Blooming*.—Medium season, very abundant, and substantially continuous.

*Tolerance to diseases*.—Very good, with no particular susceptibility to common diseases having been encountered during observations to date.

The new 'Meimonkeur' variety has not been observed under all possible environmental conditions to date. Accordingly, it is possible that the phenotypic expression may vary somewhat with changes in light intensity and duration, cultural practices, and other environmental conditions.

I claim:

1. A new and distinct Hybrid Tea rose plant characterized by the following characteristics:

(a) displays a bushy growth habit with strong vegetation, (b) forms in abundance on a substantially continuous basis attractive red-purple very double blossoms with substantially lighter non-uniform red-purple coloration on the under surface which display an anise fragrance, (c) exhibits attractive dense glossy medium green foliage, and (d) is particularly well suited for providing attractive ornamentation in parks and gardens;

substantially as shown and described.

* * * * *

Meimonkeur